United States Patent
Sansur et al.

(10) Patent No.: US 12,274,811 B2
(45) Date of Patent: Apr. 15, 2025

(54) DURAL REPAIR DEVICE AND METHOD OF USE

(71) Applicant: UNIVERSITY OF MARYLAND, BALTIMORE, Baltimore, MD (US)

(72) Inventors: Charles Sansur, Towson, MD (US); Steven C. Ludwig, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 18/205,099

(22) Filed: Jun. 2, 2023

(65) Prior Publication Data

US 2023/0310168 A1 Oct. 5, 2023

Related U.S. Application Data

(62) Division of application No. 16/646,329, filed as application No. PCT/US2018/050730 on Sep. 12, 2018, now Pat. No. 11,672,672.
(Continued)

(51) Int. Cl.
*A61F 2/02* (2006.01)
*A61B 17/80* (2006.01)
(Continued)

(52) U.S. Cl.
CPC ...... *A61L 27/3675* (2013.01); *A61B 17/8028* (2013.01); *A61F 2/0063* (2013.01);
(Continued)

(58) Field of Classification Search
CPC .... A61L 2430/32; A61L 31/14; A61L 31/148; A61L 31/06; A61L 27/58; A61L 27/3675; A61L 27/14; A61B 17/7071; A61B 17/8028; A61F 2/0063; A61F 2210/0076; A61F 2250/0037; A61M 2039/0226; A61M 2039/0264; A61M 2039/027; A61M 2039/0276
See application file for complete search history.

(56) References Cited

U.S. PATENT DOCUMENTS

RE37,249 E 6/2001 Leibinger et al.
10,478,519 B2 11/2019 Nseir Manassa
(Continued)

OTHER PUBLICATIONS

International Search Report and Written Opinion for PCT/US2018/050730 mailed Nov. 19, 2018.
(Continued)

*Primary Examiner* — Dinah Baria
(74) *Attorney, Agent, or Firm* — Farber LLC

(57) ABSTRACT

Dural repair devices that are configured to effectively and reliably repair the damage of a dural tear due to incidental durotomies are provided, along with methods of use. The devices and methods enhance the ability of a surgeon to repair a patent's dura mater, or dura, during surgery of the central nervous system. The dural repair device has a multi-layer structure configured to exert a pressure or tamponade effect to compress a patient's dura to its state prior to the spinal surgery. Thus, the dural repair devices and methods of use may reduce the patient's risk morbidity, further surgery, spinal headaches, or other injuries and discomforts.

13 Claims, 5 Drawing Sheets

Related U.S. Application Data

(60) Provisional application No. 62/557,384, filed on Sep. 12, 2017.

(51) Int. Cl.
| | | |
|---|---|---|
| *A61F 2/00* | (2006.01) | |
| *A61L 27/14* | (2006.01) | |
| *A61L 27/36* | (2006.01) | |
| *A61L 27/58* | (2006.01) | |
| *A61L 31/06* | (2006.01) | |
| *A61L 31/14* | (2006.01) | |
| *A61B 17/70* | (2006.01) | |
| *A61F 2/30* | (2006.01) | |
| *A61F 2/44* | (2006.01) | |
| *A61M 39/02* | (2006.01) | |

(52) U.S. Cl.
CPC ............... *A61L 27/14* (2013.01); *A61L 27/58* (2013.01); *A61L 31/06* (2013.01); *A61L 31/14* (2013.01); *A61L 31/148* (2013.01); *A61B 17/7071* (2013.01); *A61F 2002/30179* (2013.01); *A61F 2002/30973* (2013.01); *A61F 2002/4435* (2013.01); *A61F 2210/0076* (2013.01); *A61F 2250/0037* (2013.01); *A61L 2430/32* (2013.01); *A61M 2039/0226* (2013.01); *A61M 2039/0264* (2013.01); *A61M 2039/027* (2013.01); *A61M 2039/0276* (2013.01)

(56) References Cited

U.S. PATENT DOCUMENTS

| | | |
|---|---|---|
| 2008/0167519 A1 | 7/2008 | St-Germain |
| 2014/0107561 A1 | 4/2014 | Dorian et al. |
| 2016/0067103 A1 | 3/2016 | Anthony |
| 2016/0095756 A1 | 4/2016 | Zurovcik |
| 2017/0072089 A1* | 3/2017 | Nseir Manassa ....... B32B 5/024 |
| 2017/0367806 A1 | 12/2017 | Gingras |

OTHER PUBLICATIONS

International Preliminary Report on Patentability for PCT/US2018/050730 mailed Mar. 26, 2020.

* cited by examiner

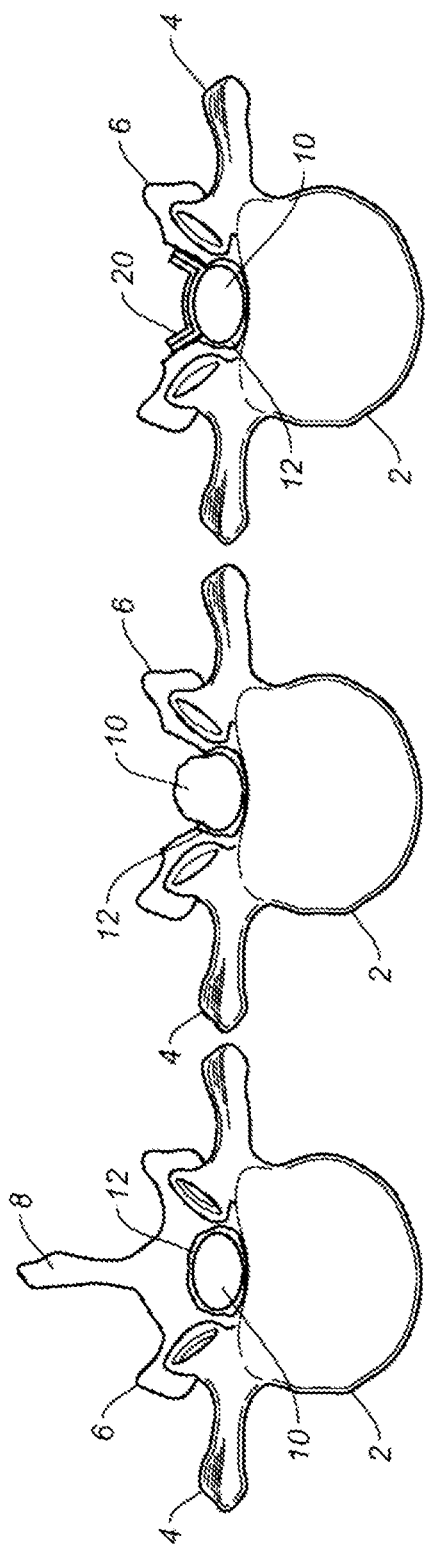
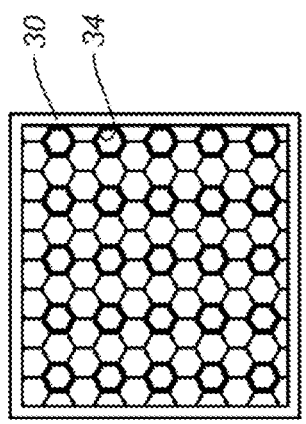
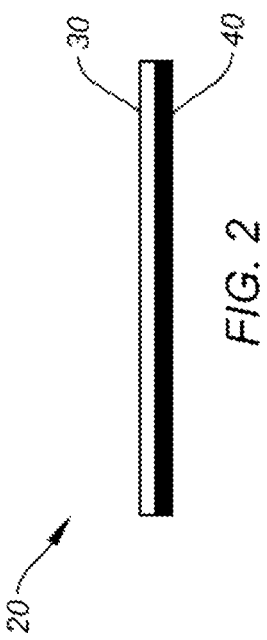
FIG. 1A  FIG. 1B  FIG. 1C
FIG. 2
FIG. 3

DURAL REPAIR DEVICE AND METHOD OF USE

CROSS-REFERENCE TO RELATED APPLICATIONS

This application is a divisional of U.S. application Ser. No. 16/646,329, which is a United States national phase application under 35 U.S.C. § 371 of International Patent Application No. PCT/US2018/050730, filed Sep. 12, 2018, which claims benefit of U.S. Provisional Application No. 62/557,384, filed Sep. 12, 2017, both the contents of which are incorporated herein by reference in their entirety. The International Application published as International Publication No. WO 2019/055551 on Mar. 21, 2019.

TECHNICAL FIELD

The present disclosure relates to a tissue sealing device and method of use, and more particularly, to a device for repairing dural or fascial defects or injuries, and/or for protecting the dura or neural elements during a surgery of the central nervous system, and related methods of use.

BACKGROUND

The dura mater, or dura, is a tough outer layer of tissue that covers and protects the brain and spinal cord. This thick membrane comprises dense irregular connective tissue and lies directly underneath the bones of the skull and vertebral column. It is the outermost of three layers of the meninges. If the dura is torn, ruptured or otherwise compromised, then cerebrospinal fluid (CSF) may persistently leak out which may cause serious complications, including severe headache, pseudomeningocele formation, nerve root entrapment, and intracranial hemorrhage.

Advancements in spinal repair devices and techniques have led to increasing numbers of spinal surgeries being performed every year. Unfortunately, one of the most common neurologic complications during spinal surgery, whether an endoscopic or open surgery such as a decompression surgery for degenerative lumbar spinal stenosis, is incidental durotomy, the unintended tear or puncture of the dura mater. This means that more incidental durotomies are occurring as a direct result of the increasing number of spine surgeries being performed, with the incidence depending on the type and complexity of the spinal procedure performed. Cerebrospinal fluid leaks which occur during surgery often result in extra time in the operating room, while cerebrospinal fluid leaks occurring after surgery may require re-operation to repair, adding more time and cost to the patient's care and leading to poor patient outcomes.

Repairing the damage of a dural tear due to an incidental durotomy can be challenging with current devices and methods due to limitations of space and because a fluid-tight closure of the patient's injured dura is necessary. Oftentimes, the only way to completely repair the defect and prevent further leakage is by suturing the hole or tear. Suturing, however, requires open surgery and is time consuming. Adhesives and patches have been developed as an alternative to sutures, and although the adhesives and patches are relatively faster than suturing to provide immediate relief of the leakage, they are not reliable for longer term treatment because the tear can reopen. Furthermore, the clinical outcome may not be compromised during the spinal surgery or during the repair. It has been observed that some adhesives and patches create further complications that impede the desired results of the underlying spinal procedure, leading to poor clinical results.

There is therefore a need for improved dural repair devices that can effectively and reliably repair the damage of a dural tear due to incidental durotomies.

BRIEF SUMMARY

The embodiments provide dural repair devices that are configured to effectively and reliably repair the damage of a dural tear due to incidental durotomies. In accordance with one embodiment, a dural repair device and method of using the device are provided. The device and method enhances the ability of a surgeon to repair a patient's dura mater, or dura, during surgery of the central nervous system. The dural repair device has a multi-layer structure configured to exert a pressure or tamponade effect to compress a patient's dura to its state prior to the spinal surgery. Thus, the dural repair device and method of using may reduce the patient's risk morbidity, further surgery, spinal headaches, or other injuries and discomforts. The dural repair device can be provided with associated instrumentation, a suture material, a set of needles, and a set of suture anchors. The dural repair device may also include an automated dural sewing device.

In accordance with an exemplary embodiment of the present disclosure, a tissue sealing device is provided that comprises a multi-composite plate having a top layer and an attached bottom layer, the top layer comprising a rigid and formable resorbable thermoplastic material, the bottom layer comprising a softer and compressible material, wherein the plate is moldable under heat treatment and is configured to provide a water-tight seal over a treatment site. The tissue sealing device may further include a hole for placement of a bone fastener therethrough. Additionally or alternatively, the plate may be attachable to the treatment site with sutures. For instance, in one embodiment, the softer bottom layer can be sutured to the treatment area, such as to the dura.

In some embodiments, the tissue sealing device may include a valvular pore for insertion of a needle therethrough. The valvular pore may include a thickened portion of the bottom layer.

In some embodiments, the top layer and bottom layer are adhered together. In other embodiments, the top layer and bottom layer attach together by a friction fit. For example, the top layer may comprise apertures and the bottom layer may comprise studs for engaging the apertures of the top layer.

In some embodiments, the top layer and bottom layer are detachable from one another. The bottom layer may also be larger in surface area than the top layer in some embodiments. In still other embodiments, the top layer and bottom layer differ in size or shape. The plate may be configured to be cut to a desired shape or size.

According to one aspect, the heat treatment may comprise warm water treatment.

According to another aspect, the bottom layer may be configured to adhere to the treatment site.

Suitable thermoplastic materials may be selected from the group consisting of polylactic acid (PLA), poly-L-lactic acid (PLLA), polyglycolic acid (PGA), poly-P-dioxanone, poly-E-caprolactone, polyorthoester, poly-B-hydroxybutyrate, poly-B-hydroxyvalerate, poly-DTH-iminocarbonate, and L-lactide-co-glycolide.

Suitable compressible materials may be selected from the group consisting of collagen, or a collagen matrix-like substance, polyester urethane, polysaccharide, poly(lacticco-glycolic acid) (PGLA) poly-p-dioxanone (PDS), cellulose, human skin, and bovine pericardium.

It is contemplated that the treatment site may be at a laminar defect of a spine, at a cranial defect of a skull, or at a repair site of a fascia.

In accordance with another embodiment of the present disclosure, a method of sealing a treatment site is provided. The method may include providing a multi-composite plate having a top layer and an attached bottom layer, the top layer comprising a rigid and formable resorbable thermoplastic material, the bottom layer comprising a softer and compressible material, the plate being moldable under heat treatment and being configured to provide a water-tight seal over a treatment site; forming a sealing device from the multi-composite plate; and securing the formed sealing device to the treatment site.

According to one aspect, the step of forming the sealing device includes application of a heat treatment, and the heat treatment may include warm water.

The step of forming the sealing device may include cutting the plate to a desired size or shape. The step of forming the sealing device may also include molding the plate into a desired shape.

The step of securing the sealing device may include suturing the sealing device to the treatment site. The step of securing the sealing device may also include inserting a bone fastener through the sealing device to the treatment site. Additionally the step of securing the sealing device may also apply a tamponade pressure effect to the treatment site.

It is contemplated that the treatment site may be at a laminar defect of a spine, at a cranial defect of a skull, or at a repair site of a fascia.

BRIEF DESCRIPTION OF THE DRAWINGS

FIG. 1A illustrates a patient's spine and dura in a normal state prior to removal of bone during a spinal surgery.

FIG. 1B illustrates the patient's spine of FIG. 1A in a decompressed state after removal of bone during a spinal surgery.

FIG. 1C illustrates the patient's spine of FIG. 1B with a dural repair device according to one embodiment of the present disclosure.

FIG. 2 is a side view of the dural repair device of FIG. 1C.

FIG. 3 is a top-down view of the dural repair device of FIG. 2.

DETAILED DESCRIPTION

Figure 4:
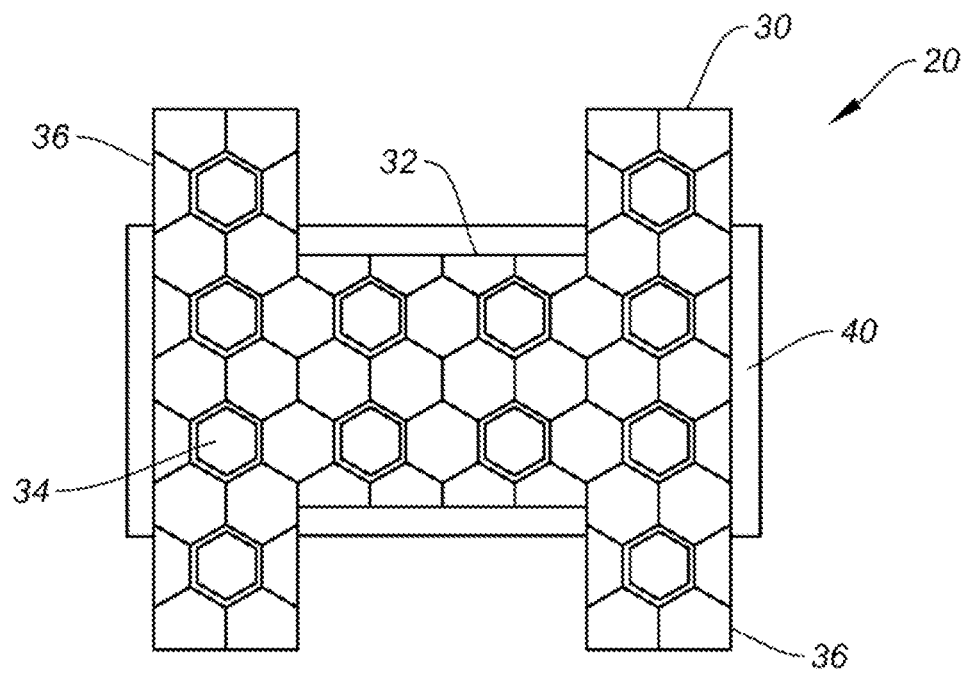
FIG. 4 is a top-down view of a dural repair device according to another embodiment of the present disclosure.

The present disclosure provides a tissue sealing device and method of using such a device for wound repair. More particularly, the present disclosure provides a dural repair device that is configured for repairing dural tears due to incidental durotomies. The dural repair device 20 of the present disclosure comprises a moldable and resorbable plate configured to facilitate dural closure during a spinal surgery or cranial surgery. Furthermore, the dural repair device 20 may be used during non-spinal or cranial procedures in which the dura is inadvertently injured, and requires repair, or during surgeries in which the dura is intentionally opened to address intradural pathology, and then requires subsequent closure. The dural repair device 20 has a multi-layer structure made of materials that are approved for use with dural repairs. The dural repair device 20 is configured to exert a pressure or tamponade effect to compress a patient's dura 12 to its normal state prior to spinal surgery, as further described below.

Turning now to the drawings. FIGS. 1A-1C illustrate a method of using an exemplary dural repair device 20 of the present disclosure. FIG. 1A shows a patient's spine, in cross-sectional view, in a normal state prior to surgery. The vertebral body 2, transverse processes 4, inferior articular processes 6, and spinous process 8 are all in their proper position. The spinal cord and cerebrospinal fluid 10 are well protected within the intact dura mater, or dura, 12. After a decompression surgery to remove bone tissue, as shown in FIG. 1B, the dura mater 12 may be compromised by an inadvertent tear or breach occurring during the spinal surgery, or the dura 12 may expand as shown, which then allows cerebrospinal fluid to leak out. A dural repair device 20 may be applied as shown in FIG. 1C, to restore the dura 12 back to normal and keep the cerebrospinal fluid 10 from leaking out.

In accordance with one aspect of the disclosure, the dural repair device 20 may have a thickness in the range of approximately 3 millimeters to 4 millimeters, although dural repair devices 20 having other thicknesses may be used accordingly. As shown in FIG. 2, the dural repair device 20 may include two layers: a top layer 30 and a bottom layer 40. In one embodiment, the top layer 30 is pre-attached to the bottom layer 40. The top layer 30 and the bottom layer 40 may be attached by an adhesive, such as a biological glue or the like, by an adhesive process, such as forming or pressure fitting, or by an interference fit (see FIGS. 6A-6C), or the like. The dural repair device may be moldable to fit into a space to support the patient's dura 12, such as in a patient's laminar defect, or space that was occupied by bone prior to bone removal, and to pro % ide a fluid-tight closure to reduce the likelihood of cerebrospinal fluid leakage.

At least one layer of the multi-layer structure of the dural repair device 20 is rigid, and at least one layer of the multi-layer structure is pliable or conformable. The dural repair device 20 of the present embodiment may be formable by heat-forming. For example, and as further described below, at least one layer of the multi-layer structure is heat-formable to adapt a desired shape, such as the shape of a patient's laminar defect (see FIGS. 1B and 1C; see also FIGS. 8A-10B). According to one embodiment, the dural repair device 20 is heat-formable by placing the dural repair device 20 in a warm bath and forming the dural repair device 20 into a desired shape by hand. Alternatively, the dural repair device 20 may be formed by using a template of the desired shape, such as a moldable metal template or the like, and using the template in the warm bath to form the desired shape. Furthermore, the dural repair device 20 may be cut to fit into the space of the patient's laminar defect, or alternatively to fit into the space of the patient's laminar defect and provide a friction fit within the laminar defect, as further described below.

The dural repair device 20 of the illustrated embodiment may be held in place by fasteners 60, such as by screws or suture anchors that are inserted into the dural repair device 20 and bone, to anchor the dural repair device 20 to the bone and support the patient's dura 12 (see FIGS. 8A, 8B, 9A, and 10B). The fasteners 60 are inserted and fastened in holes or apertures preformed in the dural repair device 20. Alternatively, the dural repair device 20 may be moldable to fit into the space and molded to frictionally fit within the laminar defect between the bone and dura 12, without the use of fasteners. Thus, a rigid thermoplastic material is formable, such as heating in a warm bath as described above, and molded to fit into the space produced by the bone removal during spinal surgery.

The top layer 30 of the dural repair device 20 is configured to exert a pressure or tamponade effect to compress the patient's dura 12 to its state prior to the spinal surgery. In the illustrated embodiment, the top layer is a rigid and formable material that is bioabsorbable or resorbable. For example, the top layer 30 in the illustrated embodiment may be a thermoplastic, such as polylactic acid (PLA), poly-L-lactic acid (PLLA), polyglycolic acid (PGA), poly-P-dioxanone, poly-E-caprolactone, polyorthoester, poly-B-hydroxybutyrate, poly-B-hydroxyvalerate, poly-DTH-iminocarbonate, or L-lactide-co-glycolide, or the like. The material of the dural repair device 20 of the present embodiment generally has preferred bioabsorbability, rather than mechanical properties such as tensile strength, since many dural injuries caused by spinal surgery are commonly repaired within 2-3 weeks. Thus, the dural repair device 20 is configured to be reabsorbed within 1 month or within 1-6 months of the injury caused by spinal surgery.

The bottom layer 40 is made of a softer material than the top layer 30. In one embodiment, the bottom layer 40 of the dural repair device 20 is a collagen-like material that is configured to be compressed by the top layer 30 to fill gaps between the top layer 30 and the patient's dura mater 12. For example, the bottom layer 40 can be made of collagen, or a collagen matrix-like substance, such as commercially-available Duragen™ (Integra), Durepair® (Medtronic, Inc.), Duramatrix® (Stryker, Inc.), polyester urethane, polysaccharide, poly(lactic-co-glycolic acid) (PGLA) poly-p-dioxanone (PDS), cellulose, or human skin, bovine pericardium, or the like. In use, the rigid and formable top layer 30 compresses the pliable bottom layer 40 into the desired shape to substantially seal the laminar defect and provide a fluid-tight closure. The bottom layer 40 supports the patient's dura 12, and as described above, is fixed to the patient's surrounding bone with the top layer 30. This softer bottom layer 40 can be sutured to the treatment area, such as directly to the dura.

Figure 5A:
FIG. 5A is a side view of the dural repair device of FIG. 1C having a valvular pore, according to another embodiment of the present disclosure.
Figure 5B:
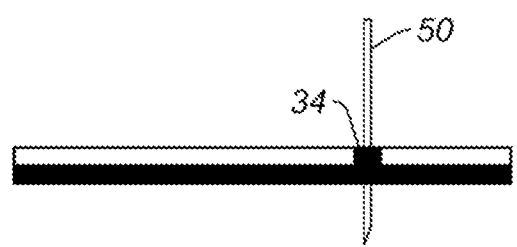
FIG. 5B shows the dural repair device of FIG. 5A in use with a needle.

According to another embodiment, the dural repair device 20 further includes a valvular pore 34 configured to provide one-way fluid flow for filling the thecal sac of the patient's dura 12. The valvular pore 34 includes a thickened portion of the bottom layer 40 such that the thickened portion prevents fluid from flowing out of the dura 12 when a needle 50 is passed through the dural repair device 20, as shown in FIGS. 5A and 5B. Alternatively, the valvular pore 34 may include a dynamically translating membrane that is positioned in different planes to allow for introduction and simultaneous containment of added cerebral spinal fluid. For example, the surgeon may fill the patient's thecal sac with a cerebrospinal fluid-like fluid through the valvular pore 34 to provide an enhanced tamponade effect. The cerebrospinal fluid-like fluid and enhanced tamponade effect may improve healing of the dura 12, and increase adherence of the dural repair device 20 to the dura, to improve sealing the laminar defect for a fluid-tight closure, and to potentially reduce the risk and/or severity of discomforts such as spinal headaches.

The dural repair device 20 may be provided in a typical shape and size, such as shape and size that may be applicable for a common laminar defect in a common patient spinal canal. A typical shape may be a square or rectangle, as shown in FIG. 3. Other shapes include an H-like shape as shown in FIG. 4, which illustrates the dural repair device 20 having a pre-formed H-like shape in which the body of the device 20 includes a central portion 32 and flaps 36. Of course, it is understood that other pre-formed shapes may be used, such as for example, a circle, semicircle, or oval. Thus, a surgeon may have a set of dural repair devices 20 having various pre-formed shapes and pre-cut sizes for many common dural and fascial defects and many common patient's spinal canals. Since the dural repair device 20 can be cut and shaped to specificity, it is also understood that the device 20 may be provided as a large sheet, a strip, or roll of material that can then be cut and shaped to suit the patient's needs, as will be described further below.

Forming the dural repair device 20 further includes heating the dural repair device 20, molding the dural repair device 20 to a desired shape, and cutting the dural repair device 20 a desired size. In the current embodiment, heating the dural repair device 20 includes placing the dural repair device 20 in a warm bath, and molding the dural repair device 20 includes hand-molding the dural repair device 20.

Furthermore, securing the dural repair device 20 to the laminar defect includes substantially sealing the laminar defect for a fluid-tight closure by positioning a pliable bottom layer of the dural repair device 20 adjacent to the patient's dura (see also FIGS. 8-11). In the illustrated embodiment, securing the dural repair device 20 further includes fastening the dural repair device 20 to bone adjacent to the laminar defect such as with fasteners 60, or in the alternative, frictionally fitting the dural repair device 20 within the laminar defect formed by the bone adjacent to the patient's dura 12.

Figures 6A, 6B, 6C:
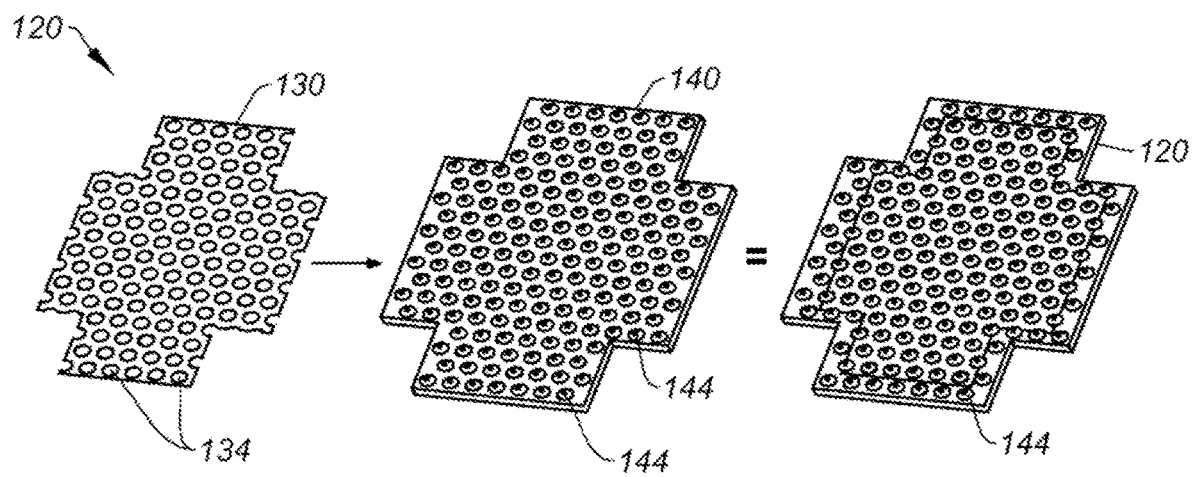
FIGS. 6A-6C show an exploded view of a dural repair device, according to another embodiment of the present disclosure.

In another embodiment shown in FIGS. 6A-6C, the dural repair device 120 may be configured in multiple layers that are coupled using an interference or friction fit. For example, as shown in FIGS. 6A and 6B, the bottom layer 140 includes a plurality of studs 144 generally arranged in a pattern, and the top layer 130 includes a plurality of apertures 134 that are generally arranged in the same pattern as the plurality of studs 144. As a further example, the bottom layer 140 is pliable, while the top layer 130 is relatively stiff such that the bottom layer 140 takes the shape of the top layer when coupled. As discussed above, the top layer 130 can be molded to a desired shape. The plurality of apertures 134 of the top layer 130 and the plurality of studs 144 of the bottom layer 140 are aligned and coupled together by firmly pressing, as shown in FIG. 6C.

In some embodiments, the softer, pliable layer can be detached from the harder top layer in situations where extra redundancy of the softer layer could be used to fill in voids in the latter recesses of the spine or parts of the anatomy that are difficult to reach. In such a case, the device 20 may be used with a smaller hard layer that is secured to bone or other tissue, and a larger soft layer to cover broader areas where lamina or skull is still present such that the smaller hard layer covers the area where bone is not present, and the soft layer that extends beyond the hard layer can be tucked underneath the lamina or skull.

The present disclosure provides a method of using the dural repair device 20, such as described above, in a laminar defect of a patient during a spinal surgery. The method of the current embodiment includes providing the dural repair device 20 configured to fit within a laminar defect of a patient during a spinal surgery, forming the dural repair device 20 to the laminar defect, and securing the dural repair device 20 to the laminar defect.

Figure 7:
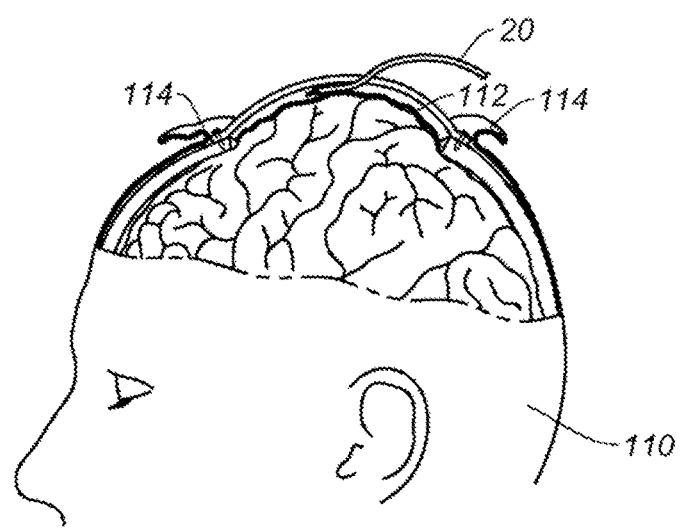
FIG. 7 shows the dural repair device of FIG. 1C applied to a cranium after decompressive craniectomy.

In another exemplary method of using the dural repair device 20, FIG. 7 illustrates a patient after a craniectomy who is vulnerable to brain injury due to the absence of a portion of the skull 110 for protection. The dural repair device 20 of the present disclosure may be applied in this situation to seal and protect the vulnerable portion of the brain 112, as shown in which the device 21 can be applied over the brain 112 prior to closing up the skull flaps 114 over the device 20. The device 20 may be configured for use with a drain and/or a pressure monitor, if so desired.

Figure 8A:
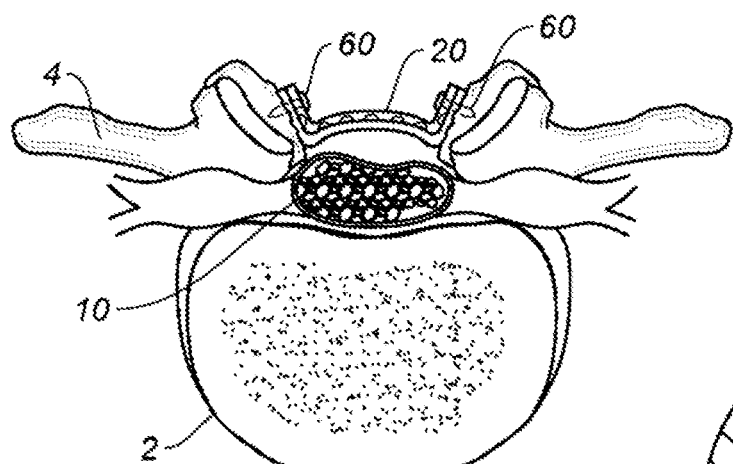
FIG. 8A shows the dural repair device of FIG. 1C in use in a patient's spine.
Figure 8B:
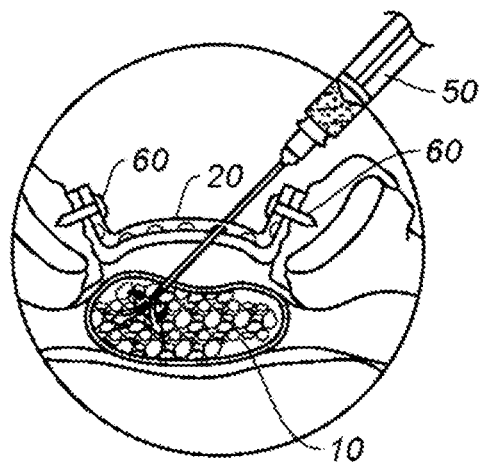
FIG. 8B is an enlarged view showing a needle injecting fluid through the valvular pore of the dural repair device of FIG. 8A.

FIGS. 8A to 10B illustrate exemplary methods of using the dural repair device 20 of the present disclosure after spinal surgery to restore the dura 12. As shown in FIG. 8A, the dural repair device 20 may be molded and formed, then secured to bone using fasteners 60, to ensure that the spinal cord and cerebrospinal fluid 10 are protected and do not leak. If desired, the surgeon may fill the patient's thecal sac with a cerebrospinal fluid-like fluid by injecting with syringe 51 through the valvular pore 34 to provide an enhanced tamponade effect, as shown in FIG. 8B. The cerebrospinal fluid-like fluid and enhanced tamponade effect may improve healing of the dura 12, and increase adherence of the dural repair device 20 to the dura, to improve sealing the laminar defect for a fluid-tight closure, and to potentially reduce the risk and/or severity of discomforts such as spinal headaches.

Figure 9A:
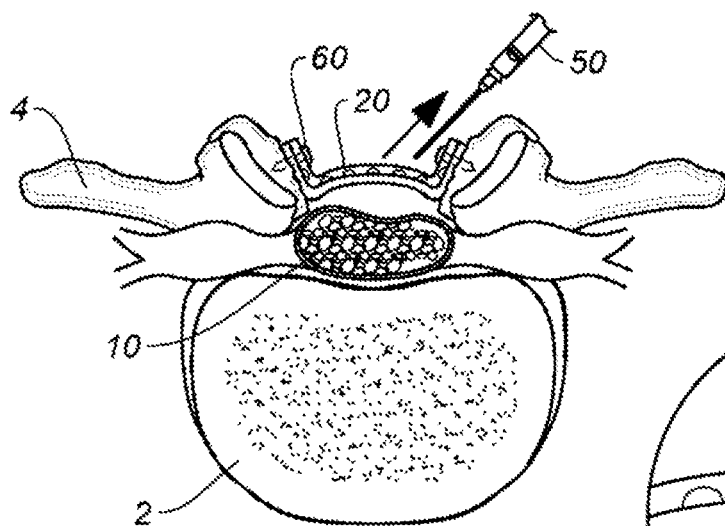
FIG. 9A shows the dural repair device of FIG. 1C in use in a patient's spine along with an injection needle.
Figure 9B:
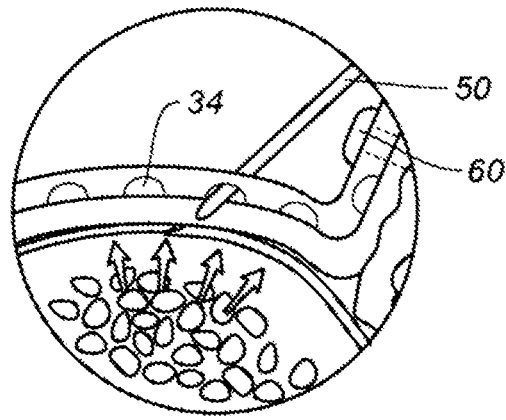
FIG. 9B is an enlarged view showing a needle removing fluid through the valvular pore of the dural repair device of FIG. 9A.

FIGS. 9A and 9B illustrate an exemplary method of using the dural repair device 20 of the present disclosure after spinal surgery to restore the dura 12, while also allowing removal of fluid or fluid-like materials. As shown in FIG. 9A, the dural repair device 20 may be used with a syringe 50 for removal of fluids or fluid-like materials. A needle of the syringe 50 can be inserted through valvular pore 34 to withdraw materials out of the patient and away from the dural repair device 20 as shown in FIG. 9B.

Figure 10A:
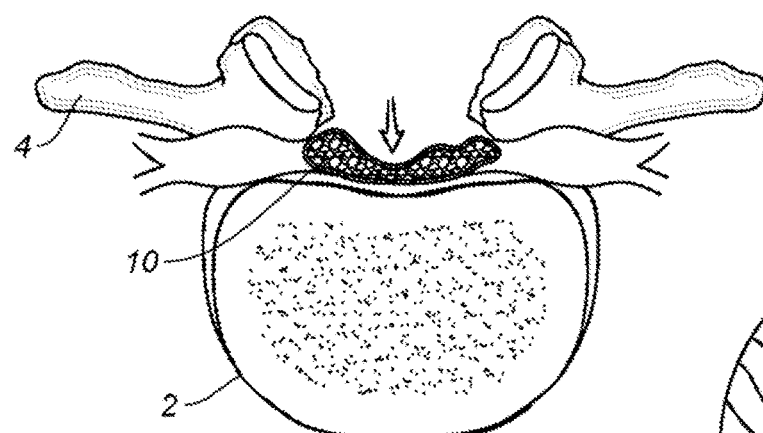
FIG. 10A is a perspective view of a patient's spine having an unprotected and vulnerable neural element after spinal surgery.
Figure 10B:
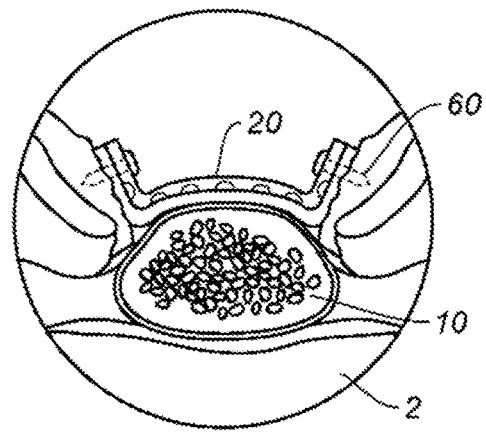
FIG. 10B is an enlarged view of the patient's spine of FIG. 10A after the application of the dural repair device of FIG. 1C.

FIGS. 10A and 10B illustrate an exemplary method of using the dural repair device 20 of the present disclosure to provide neural protection from post operative hematoma or seroma. In some scenarios in brain and spine surgery where the dura 12 may be intact, there is a need to provide additional protection to the brain, spinal cord or nerve roots due to the risk of compression from blood clots and fluid collections that may build up because the patient is on blood thinners, or has fluid overload. In these high risk patients, this device 20 provides the surgeon with a means of protecting the neural elements, even when there is no need to repair or seal the dura. As shown in FIG. 10A, the dura 12 is still intact after removal of bone during spinal surgery. However, as shown in FIG. 10B, the dural repair device 20 can be applied to further protect the area, and secured with bone fasteners 60.

Aside from dural repair and dural/nerve protection, the device 20 of the present disclosure could also be used to help reinforce the fascia of the back and abdomen. For example, the device 20 may serve as a barrier to adhesion formation for wounds that are expected to be re-opened, and therefore has applications for all sites of the human body.

Figure 11A:
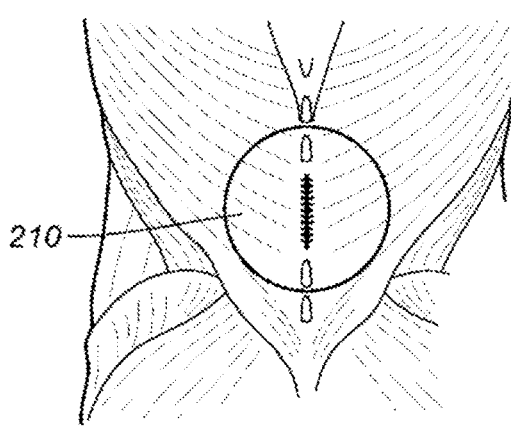
FIG. 11A illustrates a repaired wound site on a patient's fascia.
Figure 11B:
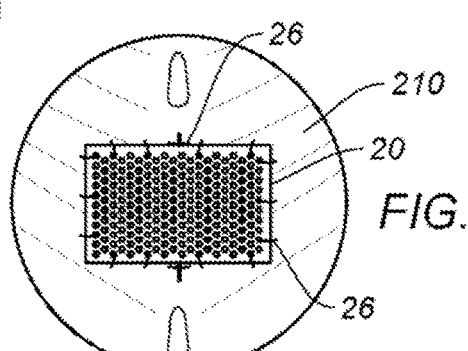
FIG. 11B is an enlarged view of a tissue sealing device in accordance with an exemplary embodiment of the present disclosure in use with the repaired wound site of FIG. 11A.
Figure 11C:
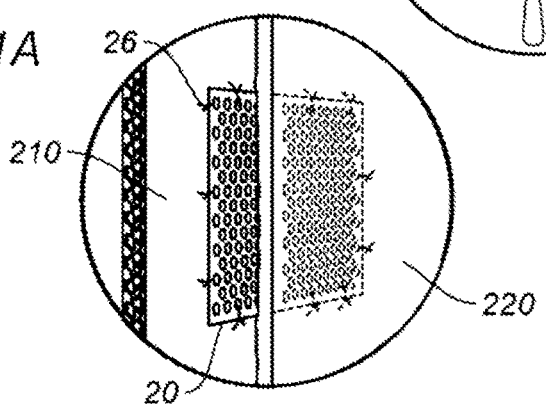
FIG. 11C is a partial cutaway view of the tissue sealing device and wound site of FIG. 11B.

Referring now to FIGS. 11A-11C, in still another embodiment the dural repair device 20 can be applied to provide a dural seal. For example, in complex cases in which there is limited confidence about watertight seal, the dural repair device 20 serves as a wound repair or wound sealing device. In the illustrated example, the device 20 can be applied to the fascia as a second barrier to CSF leakage. For instance, as shown in FIG. 11A, after spinal surgery has been completed and the wound area 210 sutured shut, the tissue sealing device 20 may be applied over the sutured area with sutures 26, as shown in FIGS. 11B and 11C. This tissue sealing device 20 thus serves to protect the area by providing an additional watertight seal over the fascia and behind the patient's skin 220.

In still another example, the tissue sealing device 20 of the present disclosure could be used during skull base surgery where dural leaks are common and there is a need to seal the dura with a device that has a soft inner lining, and a moldable outer shell that can be cut down to the appropriate size as would be the case for pituitary surgery where CSF leaks occur very commonly.

Although the discussion focuses on the spine and brain, it will be appreciated that many of the principles may equally be applied to other structural body parts within a human or animal body.

Other embodiments of the disclosure will be apparent to those skilled in the art from consideration of the specification and practice of the disclosure provided herein. It is intended that the specification and examples be considered as exemplary only.

What is claimed is:

1. Method of sealing a treatment site for a dural repair, comprising:
   providing a dual layer, multi-composite plate having a top layer and an attached bottom layer, the top layer comprising a rigid and formable resorbable thermoplastic material, the bottom layer comprising a compressible material softer than the thermoplastic material of the top layer, the plate being moldable under heat treatment and being configured to provide a water-tight seal over a treatment site, wherein the plate includes a valvular pore for insertion of a needle therethrough, the valvular pore being configured to provide one-way fluid flow;
   forming a sealing device over the treatment site from the multi-composite plate; and
   securing the formed sealing device to the treatment site.

2. The method of claim 1, wherein the step of forming the sealing device includes application of a heat treatment.

3. The method of claim 2, wherein the heat treatment includes warm water.

4. The method of claim 1, wherein the step of forming the sealing device includes cutting the plate to a desired size or shape.

5. The method of claim 1, wherein the step of forming the sealing device includes molding the plate into a desired shape.

6. The method of claim 1, wherein the step of securing includes suturing the sealing device to the treatment site.

7. The method of claim 1, wherein the step of securing includes inserting a bone fastener through the sealing device to the treatment site.

8. The method of claim 1, wherein the step of securing applies a tamponade pressure effect to the treatment site.

9. The method of claim 1, wherein the treatment site is at a laminar defect of a spine.

10. The method of claim 1, wherein the treatment site is at a cranial defect of a skull.

11. The method of claim 1, wherein the treatment site is at a repair site of a fascia.

12. The method of claim 1, wherein the treatment site includes a neural element.

13. The method of claim 12, wherein the neural element comprises a brain, spinal cord, or nerve root.

* * * * *